United States Patent [19]

Walker

[11] Patent Number: 5,291,904
[45] Date of Patent: Mar. 8, 1994

[54] DORSIFLEXION ASSISTING DEVICE FOR HEMIPLEGICS

[76] Inventor: Marshall Walker, 72 Friern Barnet Lane, London N11 3NB, England

[21] Appl. No.: 897,940

[22] Filed: Jun. 15, 1992

[30] Foreign Application Priority Data

Jun. 19, 1991 [GB] United Kingdom ............... 9113232

[51] Int. Cl.⁵ ........................... A61F 5/37; A61F 5/00
[52] U.S. Cl. ....................... 128/882; 602/23; 602/27
[58] Field of Search ............ 128/882, 869, 876; 602/5, 23, 24, 26, 27, 32, 36, 38, 40, 62, 63

[56] References Cited

U.S. PATENT DOCUMENTS

| | | | |
|---|---|---|---|
| 604,044 | 5/1898 | Hibbert | 602/27 |
| 1,072,369 | 9/1913 | Spahn | 602/27 |
| 1,332,047 | 2/1920 | Lasher | 602/27 |
| 2,107,095 | 2/1938 | Wagner | 602/23 |
| 2,485,036 | 10/1949 | Christopher | 602/23 |
| 2,522,853 | 9/1950 | Black | 602/23 |
| 2,594,227 | 4/1952 | Smith | 602/23 |
| 2,656,834 | 10/1953 | Hatkoff | 602/27 |
| 3,958,567 | 5/1976 | Callender | 602/24 |
| 5,133,341 | 7/1992 | Singer | 602/26 |

*Primary Examiner*—Michael A. Brown
*Attorney, Agent, or Firm*—Birch, Stewart, Kolasch & Birch

[57] ABSTRACT

A dorsiflexion assisting device for Hemiplegics, comprising a first strap for extending around the calf of a wearer, a second strap for extending around an ankle region of the wearer, a connecting element extending between the first strap and the second strap, a securing member adapted to be fixed to the wearer's shoe so as to provide a securing point at the outer side of the shoe, at or forward of the instep region thereof, and a connecting member extending between the second strap and the said securing point, one or both of the connecting element and the connecting member being of elastic material.

6 Claims, 1 Drawing Sheet

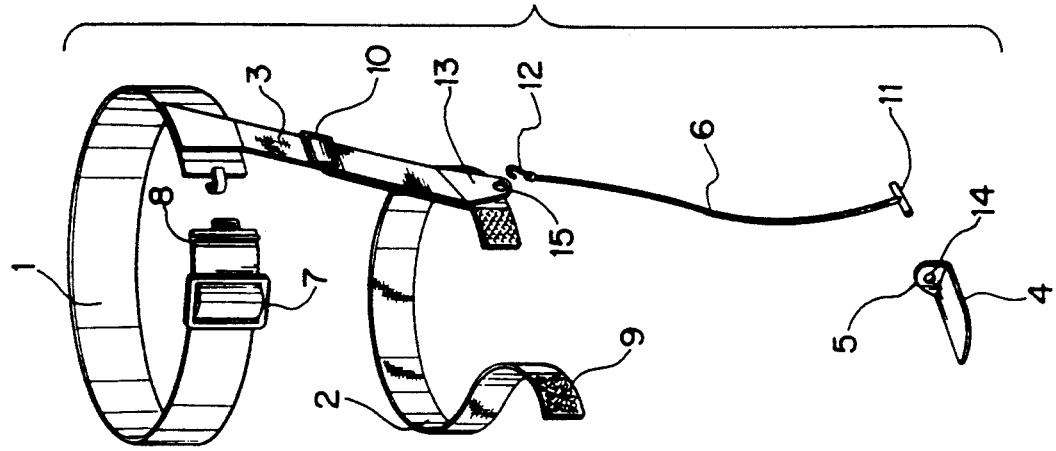
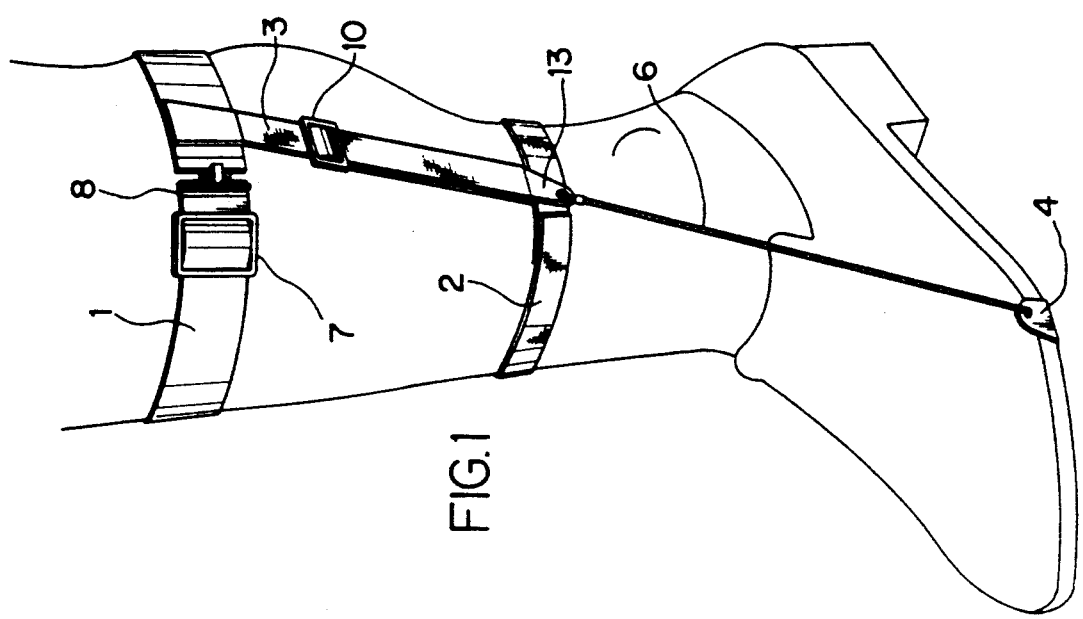

DORSIFLEXION ASSISTING DEVICE FOR HEMIPLEGICS

The invention relates to a dorsiflexion device for assisting sufferers from strokes and other Hemiplegics to walk in a more normal manner than might otherwise be possible.

In the event of a sufferer of a stroke having made a partial recovery, it is common for there to be a partial lack of control in respect of motor actions at one side of the body, for example one foot. Whereas, after partial recovery, the person may be able to stand erect and move the legs in a walking movement, an inability to raise the front of the foot with each walking step makes a proper walking action unattainable, as the front of the foot and sometimes also the outer edge of the foot tend to drag on the ground.

I have discovered that a satisfactory walking movement may be attained if, with the aid of spring means, the foot of the afflicted side of the person is biased so that the front of the foot is urged upwardly. Normally, when walking, the person would have enough strength to hold the foot in a firm contact with the ground at the appropriate times in the stride, the spring means raising the front of the foot as soon as the person begins to take a forward stride with the afflicted leg.

The person is able to walk with the sole of the foot more or less parallel to the ground, thereby being able to walk comfortably and to mount stairs without stubbing his toe on the steps. Walking is also practicable on rough ground or on uneven paving.

The invention consists in a dorsiflexion assisting device for Hemiplegics, comprising a first strap for extending around the calf of a wearer, a second strap for extending around an ankle region of the wearer, a connecting element extending between the first strap and the second strap, a securing member adapted to be fixed to the wearer's shoe so as to provide a securing point at the outer side of the shoe, at or forward of the instep region thereof, and a connecting member extending between the second strap and the said securing point, one or both of the connecting element and the connecting member being of elastic material.

The first strap is intended to be mounted around the leg at approximately mid-calf position, and the second strap mounted around the leg at a position slightly above the ankle. The connecting element is disposed at the outside of the leg, extending between the first strap and the second strap, and the said connecting member also being disposed at the outside of the leg, and extending between the second strap and the said securing point on the wearer's shoe.

The first strap should be adjustable in circumference or tailored in circumference to the particular wearer. It may have a hook type fastener or a hood-and-loop fabric Velcro type fastener, for example, by which it may be secured around the leg. Preferably, the first strap is made of soft strong cloth or other non-elastic material.

The second strap may be of elastic tape and the tape which extends between the first strap and the second strap may also be of elastic tape. This tape and the second strap combine in their actions to constitute the spring means referred to above.

Preferably, the connecting member which extends to the securing point on the wearer's shoe, is a strong non-elastic cord. The most effective action is obtained if both the second strap and the tape extending between the first strap and the second strap are of elastic material, although an adequate function is achieved if only the second strap is elastic.

The securing point for the connecting member may be provided by a mounting member fixed to the outer side of the shoe. Preferably, for obtaining a relatively inconspicuous arrangement, the securing point is provided by an adhesive backed Velcro type hook pad bonded to the sole of the shoe by the adhesive and turned up at the outer side of the shoe to provide an attachment region for the said further tape. Such a hook pad can be readily replaced when worn.

In a preferred form of the invention, the first strap has means for adjusting its length and is provided with a releasable fastener, the second strap is an elastic tape strip, the connecting element is an elastic stretch tape provided with means for adjusting its unextended length, and the connecting member is a cord having reinforced end regions one of which is engageable with the securing member at said securing point thereof, and the other of which is engageable with a securing element provided at the region where the connecting element is connected to the second strap.

Reference will now be made to the accompanying drawings which are given by way of example and which illustrate an embodiment of the invention. In the drawings:

FIG. 1 is a view of a foot and leg of a Hemiplegic person, fitted with the dorsiflexion assisting device of the invention; and FIG. 2 is a view corresponding to FIG. 1 showing the device in the unfitted (but not flattened out for packing or storage) condition.

The device comprises a first strap 1 of fabric tape having a buckle 7 or other means for adjusting its length. The strap has a releasable fastener 8 of any known kind, for example a hook type fastener, able to releasably hold the ends of the strap together so that the strap can be held around the calf of a wearer of the device, with a comfortable fit.

A second strap 2 is provided, which is of elastic stretch tape having a Velcro type fastener 9 at its ends. The strap 2 is intended to be fastened around the wearer's leg just above the ankle, as shown in FIG. 1. A connecting element 3 in the form of an elastic stretch tape extends between the first strap 1 and the second strap 2. The tape 3 has a buckle 10 or other means for adjusting its length.

At the region where the tape 3 is connected to the strap 2 a securing element 13 is provided which has an eyelet 15 in it.

A connecting member 6 in the form of a cord is provided, one end portion thereof having a T-shaped reinforcement member 11 of metal or plastics and the other end portion thereof having a cranked or bent hook type reinforcement member 12 of metal or plastics.

A securing member 4 is fixed to the sole of the wearer's shoe, somewhat forward of the instep region thereof and at the outer side of the shoe. The securing member 4 may be fixed by adhesive or by embedding, or in any other way. The securing member 4 provides a securing point 5 for the cord 6, by means of an eyelet 14. The cord 6 is passed through the eyelet 14 so that the T-shaped member 11 is retained by the eyelet. At the other end of the cord 6, bent hook member 12 is passed into the eyelet 15. If desired, instead of a bent hook member, a T-shaped reinforcement may be used also at this other end of the cord 6.

In use, the dorsiflexion assisting device functions as follows:

a) Upon taking a pace forward with the unaffected leg (the one without the device) the sole of the affected foot is in contact with the ground and the knee is forward, therefore as the distance between the end attachments of the cord 6 is shortened, the cord 6 goes slack.

b) With the weight transfer to the good leg and the upward movement of the affected leg, the affected foot will swing forward from the knee in order to take the further pace.

As the affected foot lifts from the ground, the connecting cord 6 is pulled taut and the lower strap 2 and the connecting element 3 take up the resultant tension, as the affected foot tends to fall below that which might be considered a normal position in a person unaffected by Hemiplegia. The aid thus given by the device in lifting the side/front of the foot when traversing from back to front allows the sole of the foot to travel forward more or less parallel to the ground.

c) When the heel of the affected foot touches the ground, the sole of the foot is pressed flat to the ground by the transfer of weight to that leg. This causes the lower elasticated strap 2 and the connecting element 3 to stretch further and in doing so does not affect what might be considered a normal position or posture of the foot.

d) Upon taking the next page (again with the unaffected leg) the process repeats itself, with the connecting cord 6 (and the lower strap 2 and the connecting element 3) alternately being slack or taut as one pace follows another.

I claim:

1. A dorsiflexion assisting device for Hemiplegics, comprising: a first strap for extending around the calf of a wearer, a second strap comprised of elastic material for extending around an ankle region of the wearer, a first connecting element comprised of elastic stretch material including means for adjusting an unextended length thereof and extending between and connecting the first strap with the second strap, a securing member attachable to the wearer's shoe so as to provide a securing point at the outer side of the shoe, at or forward of the instep region thereof, and a second connecting element extending between the second strap and said securing point, second connecting element being comprised of a cord having at one end a first reinforced region engageable with said securing member at said securing point, and having at the other end a second reinforced region engageable with a securing element located in the region where said first connecting element connects to the second strap.

2. The device as claimed in claim 1, wherein the first strap includes a releasable fastener and means for adjusting its length.

3. The device as claimed in claim 1 wherein the second strap comprises an elastic tape strip including a hook-and-loop fabric fastener.

4. The device as claimed in claim 1 wherein the means for adjusting the unextended length of said connecting element comprises a buckle.

5. The device as claimed in claim 1 wherein said first and second reinforced regions comprise metal or plastics reinforced ends of said cord and including means engageable in eyelets respectively located in the securing point and in the securing element.

6. The device as claimed in claim 5 wherein said means engageable in eyelets include T-shaped or bent hook-type members.